United States Patent [19]
Gimpelson

[11] Patent Number: 5,922,008
[45] Date of Patent: Jul. 13, 1999

[54] SURGICAL FORCEPS

[76] Inventor: Richard J. Gimpelson, 1028 Terrace Rock Cir., Ballwin, Mo. 63011

[21] Appl. No.: 08/920,306

[22] Filed: Aug. 28, 1997

[51] Int. Cl.[6] ............................................. A61B 17/34
[52] U.S. Cl. ...................................... 606/207; 81/418
[58] Field of Search .................... 606/1, 51, 52, 606/119, 174, 205–210

[56]          References Cited

U.S. PATENT DOCUMENTS

| D. 275,790 | 10/1984 | Marlowe . |
|---|---|---|
| 945,292 | 1/1910 | Sether . |
| 1,053,149 | 2/1913 | Blunk . |
| 1,193,987 | 8/1916 | Burdin . |
| 1,422,538 | 7/1922 | Cameron . |
| 1,659,112 | 2/1928 | Littlejohn . |
| 2,601,513 | 6/1952 | Gladstone . |
| 2,618,268 | 11/1952 | English . |
| 2,668,538 | 2/1954 | Baker . |
| 2,887,111 | 5/1959 | Leyro Diaz . |
| 4,475,544 | 10/1984 | Reis . |
| 4,600,007 | 7/1986 | Lahodny et al. . |
| 5,176,701 | 1/1993 | Desek et al. . |

*Primary Examiner*—Michael Buiz
*Assistant Examiner*—William W. Lewis
*Attorney, Agent, or Firm*—Grace J. Fishel

[57]          ABSTRACT

A surgical forceps for use in clamping vascular tissue in a body cavity where the tissue being clamped may not be in full view of an operator. The forceps have jaws of uneven length with a projection on the longer jaw starting immediately at the end and extending above the shorter jaw when the forceps are closed. The shorter jaw closes adjacent the projection, with minimal space between, thus ensuring that a selected vascular tissue is contained between the jaws and the projection.

6 Claims, 2 Drawing Sheets

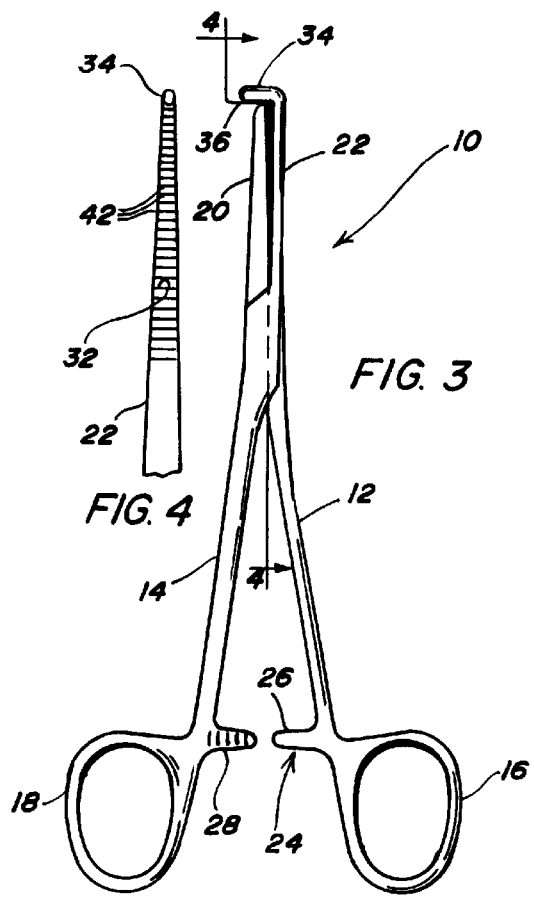
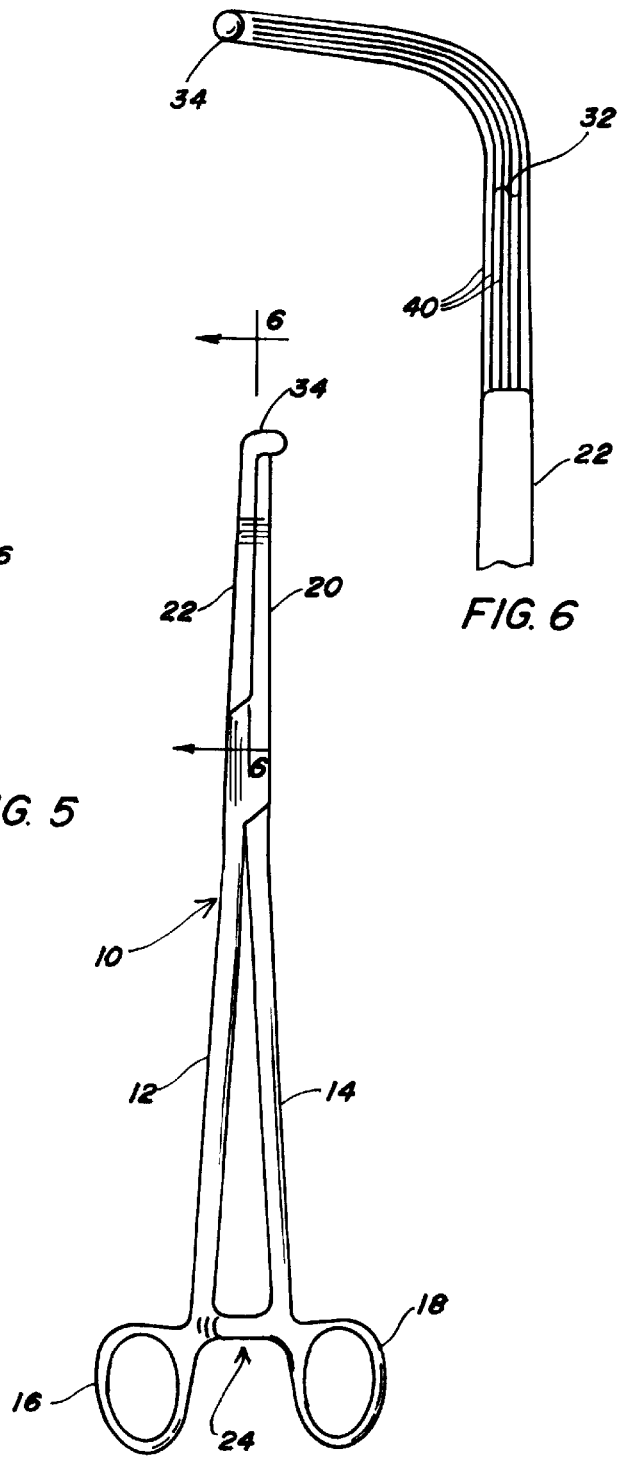

SURGICAL FORCEPS

BACKGROUND OF THE INVENTION

1. Field of the Invention

The present invention relates to surgical forceps for clamping vascular tissue in a body cavity where the tissue being clamped may not be in full view of an operator in a manner that the operator can ensure that all of the tissue is within the forceps as compressive force is applied without catching his gloved finger.

2. Brief Description of the Prior Art

In conducting surgery, for example, in a vaginal hysterectomy, after the fundus of the uterus has been delivered through an incision into the cul-de-sac, an operator can pass a finger of one hand up through the cul-de-sac and then forward over the broad ligament into the vesicouterine space. The intervening peritoneum can be torn or cut away to expose the operator's finger. During this time, the operator's finger holds back and prevents the bladder and intestines from being injured as a plurality of clamps are applied to the broad ligament. If too much traction is applied on the uterus during this stage of the procedure, the broad ligament may be torn, causing hemorrhage from the uterine artery. In a certain percentage of cases, it is difficult to bring the uterus down far enough so that the broad ligament is in full view and clamping, in these instances, is done by feel. Related clamping difficulties occur in an abdominal hysterectomy, for example, when the fallopian tubes and ovaries are to be removed. The infundibulopelvic ligament is typically clamped with a plurality of clamps, through a slit cut in the broad ligament and may not be in full view.

As the broad ligament (e.g., in a vaginal hysterectomy) or the infundibulopelvic ligament (e.g., in an abdominal hysterectomy) is clamped, an operator must determine that the entire pedicle comprising the ligament is caught within the forceps to prevent bleeding when the ligament is cut. For this purpose, the operator passes a gloved finger under and around the back side of the ligament and as the jaws of each clamp are closed around the pedicle, he palpates the tip of the clamp with a gloved finger to determine that all of the tissue is being caught in the forceps. With prior art forceps, the operator's glove may be punctured on the tip of the forceps or pinched between the jaws as compressive force is applied and torn when the operator removes his finger. It will be readily appreciated that the health of the patient and/or the operator may be compromised by an infectious disease, the vector for which is the ruptured glove.

BRIEF SUMMARY OF THE INVENTION

In view of the above, it is an object of the present invention to provide a surgical forceps that allow an operator to determine with relative ease that all of the vascular tissue to be clamped is within the forceps, having particular utility when the tissue is in a narrow or recessed workspace and may not be in full view. It is another object to provide a surgical forceps that allows an operator to determine that all of the vascular tissue is in the forceps without puncturing or tearing his glove. It is a further object to provide a surgical forceps that allow an operator to determine that all of the vascular tissue is compressed in the forceps before it is ligated and cut, thus preventing bleeding. Other objects and features of the invention will be in part apparent and in part pointed out hereinafter.

In accordance with the invention, a surgical forceps is provided for clamping vascular tissue in a body cavity where the tissue being clamped may not be in full view of an operator. The forceps include first and second elongate arms with finger grips, a ratcheting mechanism and jaws, which are conventional except that the jaws are of uneven length, with the longer jaw having a projection within which the shorter closes. In use, an operator can guide the longer jaw under the vascular tissue to be compressed and with the same finger feel for the projection to confirm that all of the tissue is between the jaws and the projection. The projection also serves to keep the operator's glove from being punctured or caught in the forceps and torn.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which several of various possible embodiments of the invention are illustrated, corresponding reference characters refer to corresponding parts throughout the several views of the drawings in which:

FIG. 3 is a plan view of the surgical forceps shown in FIG. 1;

FIG. 4 is a detail, on an enlarged scale, taken along line 4—4 in FIG. 3;

FIG. 5 is a plan view of a third surgical forceps in accordance with the present invention;

FIG. 6 is a detail, on an enlarged scale, taken along line 6—6 in FIG. 5.

DETAILED DESCRIPTION OF THE INVENTION

Figure 1:
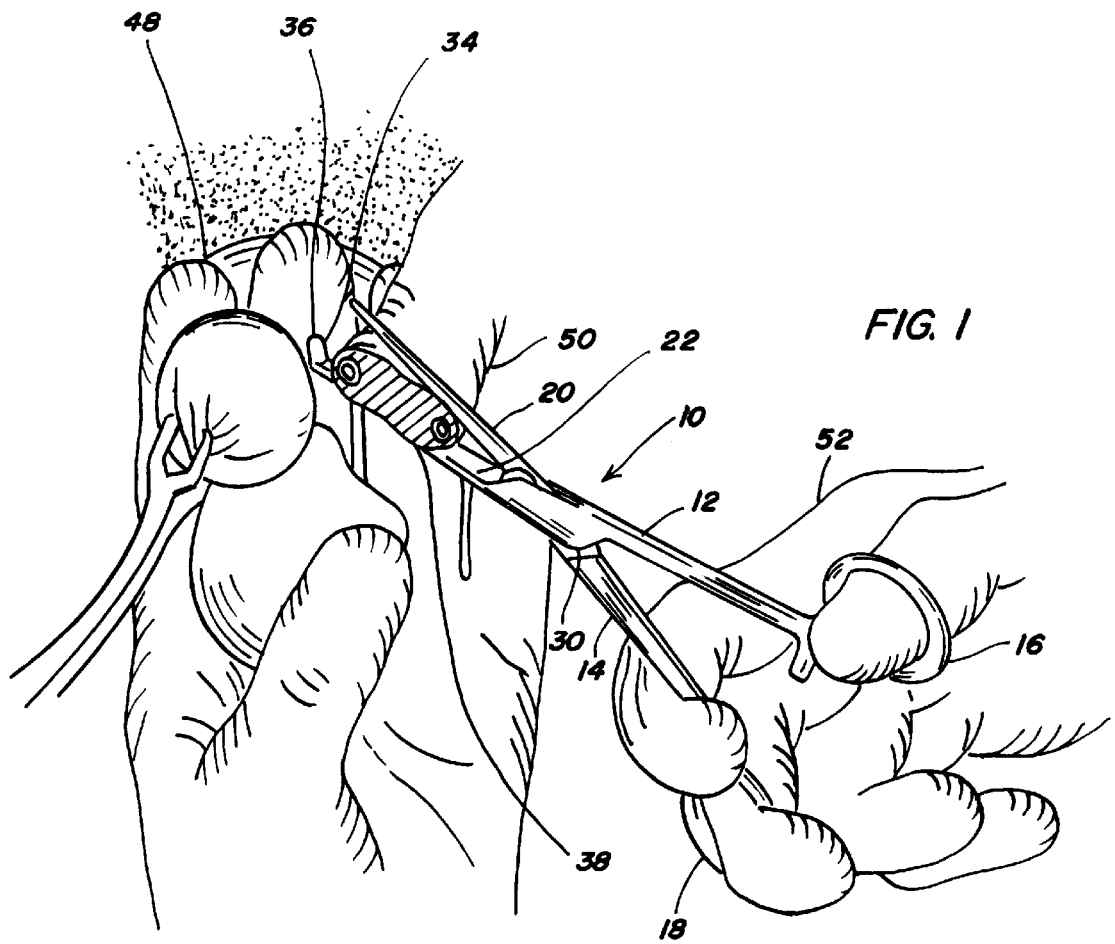
FIG. 1 is a perspective view of a surgical forceps in accordance with the present invention in use clamping a broad ligament.

Referring to the drawings more particularly by reference character, reference numeral 10 refers to a surgical forceps in accordance with the present invention. Forceps 10, as more particularly described hereinafter, are adapted for use (albeit not limited to) clamping vascular tissue in a body cavity where the tissue being clamped may not be in full view of an operator. The term "vascular tissue" includes blood vessels, in which case forceps 10 function as a hemostat, as well as pedicles of tissue containing blood vessels, forceps 10 serving as a pedicle clamp in this instance.

As shown in FIG. 3, forceps 10 are constructed from a pair of elongate arms, 12, 14, with elongate arm 12 being referred to as first arm and elongate arm 14 as second arm. First and second arms 12, 14 are pivoted in a scissors fashion about a pivot (not shown) which forms an axis of rotation. The pivot is fixedly inserted into first arm 12 and through which second arm 14 passes in a manner well known in the art of forceps making. Each of elongate arms 12, 14 have, at a proximal end thereof, first and second finger grips 16, 18, respectively, and at a distal end, first and second gripping members or jaws 20, 22, respectively. Immediately distal of first and second finger grips 16, 18 is a ratcheting mechanism 24. Ratcheting mechanism 24 comprises a ratchet arm 26 mounted on first elongate arm 12 and a ratchet catch 28 mounted on second elongate arm 14, with ratchet arm 26 and ratchet catch 28 in engaging relationship. More particularly, ratchet arm 26 and ratchet catch 28 engage each other so as to prevent finger grips 16, 18 from separating until such time as an operator applies a twisting movement in order to lift ratchet catch 28 away from ratchet arm 26. Ratcheting mechanism 24 prevents first and second jaws 20, 22 from inadvertently separating from each other. Ratchet arm 26 comprises a plurality of individual ratchet teeth against which ratchet catch 28 engage. As is well known, successive ratchet teeth are separated from each other by a substantially fixed linear distance and ratchet catch 28 can only engage ratchet arm 26 at a number of positions roughly equal to the number of individual ratchet teeth.

In order to stabilize first and second elongate arms 12, 14 laterally with respect to one another, particularly when the ratcheting mechanism is being engaged or disengaged, first and second arms 12, 14 are each provided with a crossover section 30 (FIG. 1), which is machined so that first and second arms 12, 14 cross each other along a planar interface. The planar interface is perpendicular to the pivot and cooperates with the pivot to establish the direction of relative movement between first and second arms 12, 14. Thus, when the ratcheting mechanism 24 is being operated, causing first and second arms 12, 14 to flex between the pivot and ratcheting mechanism 24, a minimum of twisting occurs at the distal end of first and second jaws 20, 22.

In the embodiment shown in FIGS. 3–4, first and second jaws 20, 22 have gripping surfaces 32. Jaws 20, 22 are rectilinear and of uneven length with a projection 34 on longer jaw 22 starting immediately at the end and extending above shorter jaw 20 when the jaws are closed. An end 36 of projection 34 functions as a guide for determining that the vascular tissue to be clamped is within forceps 10 as compressive force is applied. Shorter jaw 20 closes adjacent projection 34, with minimal space between, thus ensuring that a selected vascular tissue 38 is caught between jaws 20, 22 and projection 34. To this end, it is preferred that projection 34 be at substantially a right angle to gripping surface 32 of jaw 22 and that the spacing between the end of the shorter jaw and projection be no greater than about 1 mm. Projection 34 can be circular in cross-section or can have some other geometric shape, for example, triangular, concave on a face opposing shorter jaw 20 for complementary receipt of the distal end thereof, etc.

Jaws 20, 22 may have conventional shapes, aside from projection 34, and may be straight (FIGS. 1–4) or curved (FIGS. 5–6), to the right, left or upwardly, depending upon the purpose for which the forceps are designed. Gripping surface 32 may be smooth but is usually variously grooved 40 (FIG. 6), serrated 42 (FIG. 4), provided with a rat-tooth 44 (FIG. 2), perforated or the like. The grooves on the two jaws are laterally displaced and the serrations are longitudinally displaced, in a manner well known in the art of forceps making, so that the jaws mesh together. In like manner, a recess 46 is provided in the opposing jaw for receipt of rat-tooth 44. In other embodiments, the location of rat-tooth 44 and recess 46 may be reversed with the rat-tooth on the shorter jaw, possibly adjacent the tip, in which position the tooth would aid in the capture of the tissue to be clamped.

In order to apply a tension along gripping surface 32, which is transferred to ratcheting mechanism 24, elongate arms 12, 14 are made flexible and jaws 20, 22 are curved or outwardly bowed longitudinally. Elongate arms 12, 14 are preferably made of ordinary surgical stainless steel or the like, said material preferably being resistant to autoclaving and having a sufficient elastic range to permit the desired flexibility without permanently deforming. This flexibility, between the pivot and ratcheting mechanism 24, permits ratchet catch 28 to be separated from ratchet arm 26. It also permits bowed jaws 20, 22 to provide a firm, relatively consistent gripping spring action, along the length of gripping surface 32.

Figure 2:
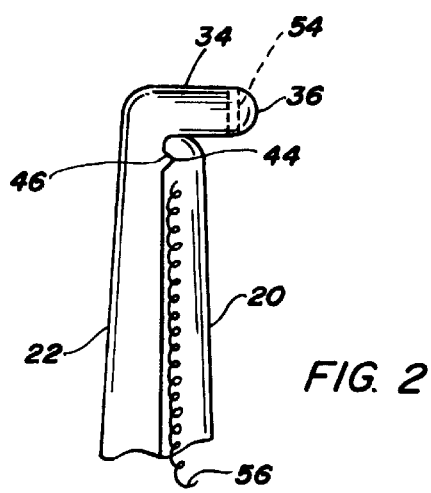
FIG. 2 is a detail, in plan and on an enlarged scale, showing the distal end of a second surgical forceps in accordance with the present invention.

In use as shown in FIG. 1, for example in a vaginal hysterectomy, after the fundus of the uterus has been delivered through an incision into the cul-de-sac, an operator can pass a finger 48 of one hand through the cul-de-sac and then forward over a broad ligament 50. The operator guides longer jaw 22 under broad ligament 50 and with finger 48 ascertains that all of the ligament is held between jaws 20, 22 and projection 34 while applying compressive force with another hand 52. As vascular tissue 38 is clamped, upwardly directed projection 34 keeps the operator's glove from being punctured by the tip of the forceps or pinched between the jaws and torn when the operator removes his hand. During this stage of the surgery, depending on the length of the broad ligaments, it may be difficult for the operator to see the distal end of forceps 10 because the uterus is still within the pelvis. Forceps 10 thus allow the operator to confirm that all of the tissue comprising the ligament is compressed in the clamp, before the ligament is ligated and cut. In a similar manner, the second broad ligament is clamped, cut and the surgery continued.

The above-mentioned use is set forth by way of illustration, not limitation, as forceps 10 can be used in other procedures in a vaginal hysterectomy or in an abdominal hysterectomy, as a hemostat and so forth, having special utility, however, when the vascular tissue is in a narrow or recessed workspace and is surrounded by delicate tissue and organs (e.g., a bladder). It will be readily appreciated that forceps 10 can be made in different sizes depending upon their intended use, and be straight or curved as described above so that the operator may act with ease. A hole 54 (FIG. 2) or a hook may be provided on projection 34 into which a thread may be threaded so as to allow the tying of the vascular tissue clamped in forceps 10. In other potential variations, jaws 20 and 22 may include an electric element 56 (FIG. 2) for cauterizing the tissue compressed within the jaws, possibly obviating the need for sutures.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A surgical forceps for clamping vascular tissue in body cavities where the tissue being clamped may not be in full view of an operator comprising first and second elongate arms pivoted in a scissors fashion first and second finger grips at a proximal end of each of the first and second arms;

a ratcheting mechanism consisting of a ratchet on the first arm adjacent to the first finger grip;

a ratchet grip on the second arm engageable with the ratch on the first arm as the finger grips are brought toward one another;

first and second jaws at a distal end of each of the first second arms, said first and second jaws having intermeshing, tissue gripping surfaces that are brought into contact as the finger grips are brought toward one another, said first and second jaws uneven length, said longer jaw terminating in a substantially right angle guide to the gripping surface projecting above the shorter jaw when the jaws are closed and said shorter jaw closing adjacent the guide with minimal space between the end of the shorter jaw and the guide for securing a tissue to be clamped between the jaws and the projection for controlling hemorrhage whereby an operator can ensure that all of the tissue be clamped is contained within the forceps when the jaws are closed by passing his gloved finger and the longer jaw of the forceps under the tissue and feeling the projection with his finger as the forceps are closed around the tissue without puncturing or tearing his glove.

2. The forceps of claim 1 wherein the distance between the guide and the shorter jaw is equal to or less than 1 mm.

3. The forceps of claim 1 wherein the first and second jaws are rectilinear.

4. The forceps of claim 1 wherein the jaws are rectilinear except at the distal end, said distal end being curved.

5. The forceps of claim 1 wherein the guide has a hole or a hook into which a thread may be threaded.

6. The forceps of claim 1 wherein at least one of the first and second jaws has an electric element for cauterizing the tissue contained within the forceps.

* * * * *